United States Patent [19]
Zebuhr

[11] Patent Number: 5,749,380
[45] Date of Patent: May 12, 1998

[54] AUTOMATED DENTAL CLEANER

[75] Inventor: William H. Zebuhr, Nashua, N.H.

[73] Assignee: Dynaproducts, Inc., Nashua, N.H.

[21] Appl. No.: 831,861

[22] Filed: Apr. 2, 1997

Related U.S. Application Data

[62] Division of Ser. No. 418,837, Apr. 7, 1995, Pat. No. 5,647,385.

[51] Int. Cl.⁶ ............................................. A45D 40/30
[52] U.S. Cl. ........................ 132/216; 132/325; 132/324; 132/322; 15/4; 15/22.1; 15/22.2
[58] Field of Search .................................. 132/322, 323, 132/324, 325, 327, 329; 15/216, 4, 22.1, 22.2, 167.2; 433/216

[56] References Cited

U.S. PATENT DOCUMENTS

| | | | |
|---|---|---|---|
| 2,093,383 | 9/1937 | Rudof et al. | 15/167.2 |
| 2,467,221 | 4/1949 | Pastl | 132/92 |
| 2,652,949 | 9/1953 | Martin | 132/308 |
| 3,421,524 | 1/1969 | Waters | 132/92 |
| 3,534,745 | 10/1970 | Waters | 132/92 |
| 3,667,483 | 6/1972 | McCabe | 132/92 |
| 3,759,274 | 9/1973 | Warner | 132/92 R |
| 3,799,177 | 3/1974 | Bragg | 132/92 |
| 3,847,167 | 11/1974 | Brien | 132/92 R |
| 3,847,168 | 11/1974 | Schlegel | 132/92 R |
| 3,886,956 | 6/1975 | Cash | 132/91 |
| 4,014,354 | 3/1977 | Garrett | 132/90 |
| 4,131,967 | 1/1979 | Northemann et al. | 15/167.2 |
| 4,235,253 | 11/1980 | Moore | 132/92 R |
| 4,245,658 | 1/1981 | Lecouturier | 132/92 A |
| 4,307,740 | 12/1981 | Florindez et al. | 132/92 R |
| 4,326,549 | 4/1982 | Hinding | 132/92 R |
| 4,338,957 | 7/1982 | Meibauer | 132/91 |
| 4,458,702 | 7/1984 | Grollimund | 132/92 A |
| 4,586,521 | 5/1986 | Urso | 132/92 R |
| 4,605,025 | 8/1986 | McSpadden | 132/92 R |
| 4,706,695 | 11/1987 | Urso | 132/92 R |
| 4,795,347 | 1/1989 | Maurer | 433/216 |
| 4,880,382 | 11/1989 | Moret et al. | 433/118 |
| 5,000,684 | 3/1991 | Odrich | 433/125 |
| 5,016,660 | 5/1991 | Boggs | 132/322 |
| 5,069,233 | 12/1991 | Ritter | 132/322 |
| 5,176,157 | 1/1993 | Mazza | 132/322 |
| 5,177,826 | 1/1993 | Vrignaud et al. | 15/22.1 |
| 5,177,827 | 1/1993 | Ellison | 15/22.1 |
| 5,305,491 | 4/1994 | Hegemann | 15/167.2 |
| 5,323,796 | 6/1994 | Urso | 132/322 |
| 5,497,526 | 3/1996 | Klinkhammer | 15/167.2 |

OTHER PUBLICATIONS

Sales brochure by Oralgiene, "A Scientific Breakthrough in Dental Hygiene", at least by Dec., 1995.

*Primary Examiner*—John J. Wilson
*Assistant Examiner*—Pedro Philogene
*Attorney, Agent, or Firm*—Brooks & Kushman P.C.

[57] ABSTRACT

The present invention automated dental cleaner includes a housing and a pair of spaced tines supported on the housing. The tines hold a length of dental floss therebetween to form a span of floss. A bracing fork having a pair of bracing tines for straddling teeth braces the dental cleaner against the teeth, thereby allowing the floss to be reciprocated by a motorized drive.

12 Claims, 10 Drawing Sheets

5,749,380

1

AUTOMATED DENTAL CLEANER

This application is a division of Ser. No. 08/418,837 filed Apr. 7, 1995 now U.S. Pat. No. 5,647,385.

RELATED DOCUMENTS

A previous disclosure document regarding the present invention was received by the U.S. Patent and Trademark Office on Apr. 8, 1993 for Disclosure No. 328956 entitled "Motor Driven Flossing Tool".

BACKGROUND

Most adults have some degree of gum disease. In an advanced form, the ailment accounts for about three quarters of lost teeth. Unhealthy gums can also lead to other health problems including serious infections.

Disease of the gums can be avoided by removal of plaque, especially from under the gum line. Brushing, alone, is not sufficient because it does not clean under the gum line between teeth. Consumer organizations have tested the available plaque removing products, including the high tech powered brushes. They report that the most important aspect of proper dental hygiene is flossing.

Proper flossing by hand, however, is an arduous and loathsome regimen. It requires dexterity and some degree of skill to properly manipulate the floss to clean all the interdental surfaces down to the attached gingiva. Dexterous people find flossing tedious and it is exceedingly difficult for the nondexterous. Consequently, an estimated 90 percent of adults have some degree of the disease in spite of efforts by their dentists to teach them how to floss.

An automated dental cleaner is, therefore, needed to reduce the amount of tedious work, perseverance, and dexterity required for proper flossing and brushing. After building and testing a variety of powered models, it was found that a practical flosser must have the following features:

(1) Means for moving a floss span between teeth with lateral strokes in order to work the floss through the tight gap or interdental contact point where adjacent teeth come in contact.

(2) Means for moving the span in both lateral and vertical directions, after passing through the tight gap, to remove plaque from interdental surfaces.

(3) Means for protecting the teeth and gums from being hammered by moving parts that reciprocate the floss span.

(4) Means for continuous replacement of the floss span.

(5) Means for preventing abrupt impact of floss against gingival tissue.

Although several powered flossers have been patented, none are able to adequately perform the functions described above. The present invention has the advantage of having the complete combination of above-mentioned features. In addition, in one preferred embodiment, the present invention includes a novel powered brush so both flossing and brushing are achieved at the same time.

SUMMARY OF THE INVENTION

The present invention provides an automated dental cleaner including a flossing fork having a pair of tines for supporting a floss span extending therebetween. The tines have guides for guiding the transfer of floss from one tine to the other. A drive for driving the floss span in a tooth cleaning motion is provided in order to clean interdental surfaces. A brace having a pair of bracing tines is also provided for straddling a tooth and bracing the cleaner against the tooth.

In preferred embodiments, the drive longitudinally drives floss between the tines in a reciprocating motion. A damper is provided for limiting the speed in which the brace can move relative to the flossing fork. This reduces the speed of user induced interdental motion of the floss span relative to gingival tissue. The damper prevents injury to gums by inhibiting over-travel of the floss span after passing through tight interdental gaps upon entry while allowing a full range of floss motion in the interdental spaces.

In another embodiment of the present invention, the flossing fork is driven in an orbital path. Orbit altering means allows the orbital path of the fork to flatten to linear side to side motion when the floss encounters resistance. The advantage being that when encountering a tight interdental gap, the floss span can "saw" its way therethrough. A floss supply spool and a floss take-up spool are arranged to be floss-connected to the fork for continuous replacement of the floss span. The drive drives both spools at continuously changing rates to compensate for changing amounts of floss on the spools so that a constant replacement rate of the floss span is maintained with constant tension of the span. A bracing and brushing fork, or BB fork, includes a pair of tines for straddling teeth and holding the cleaner thereon to stabilize the cleaner as the teeth are being flossed. Brush bristles extend inward from each BB fork tine and from a medial position on the fork to engage teeth on lingual, buccal, and top sides. The drive reciprocates the BB fork so that three dental surfaces are simultaneously brushed as the teeth are being flossed.

BRIEF DESCRIPTION OF THE DRAWINGS

The accompanying drawings in combination with the description herewith, illustrate features and advantages of the invention. Like reference numerals in different views refer to the same parts. The drawings are intended to illustrate principles of the invention and are not necessarily to scale.

DETAILED DESCRIPTION OF THE PREFERRED EMBODIMENTS

Figure 1:
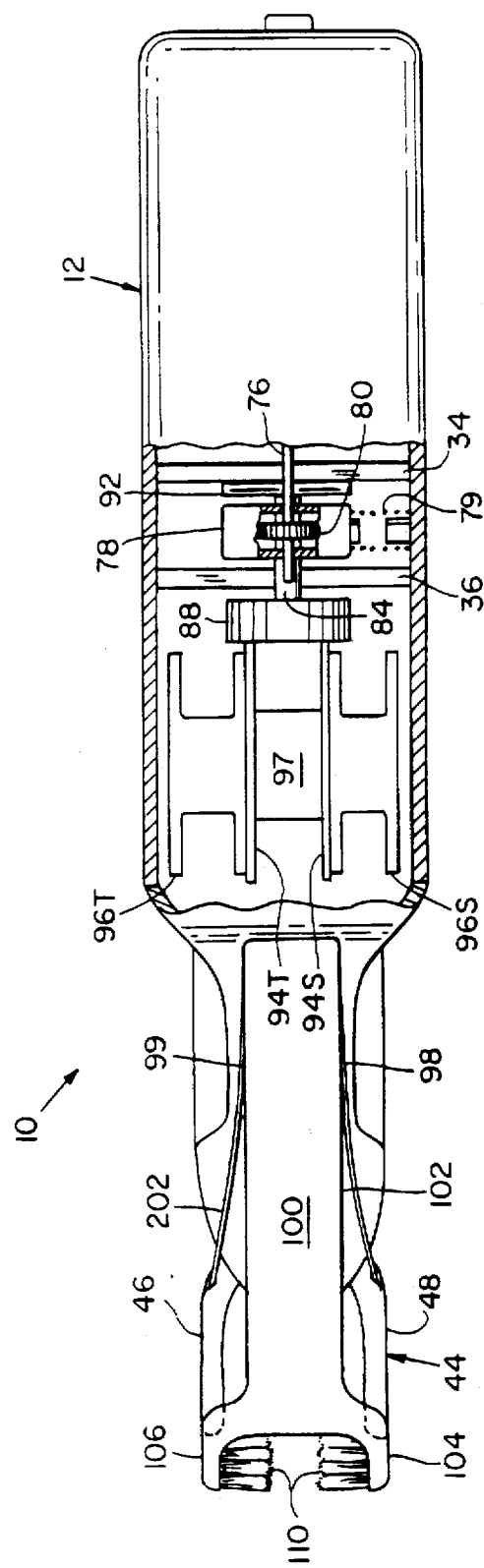
FIG. 1 is a top view, partly in section, of a preferred embodiment of an automated dental cleaner constructed in accordance with the invention with some parts removed for clarity.
Figure 2:
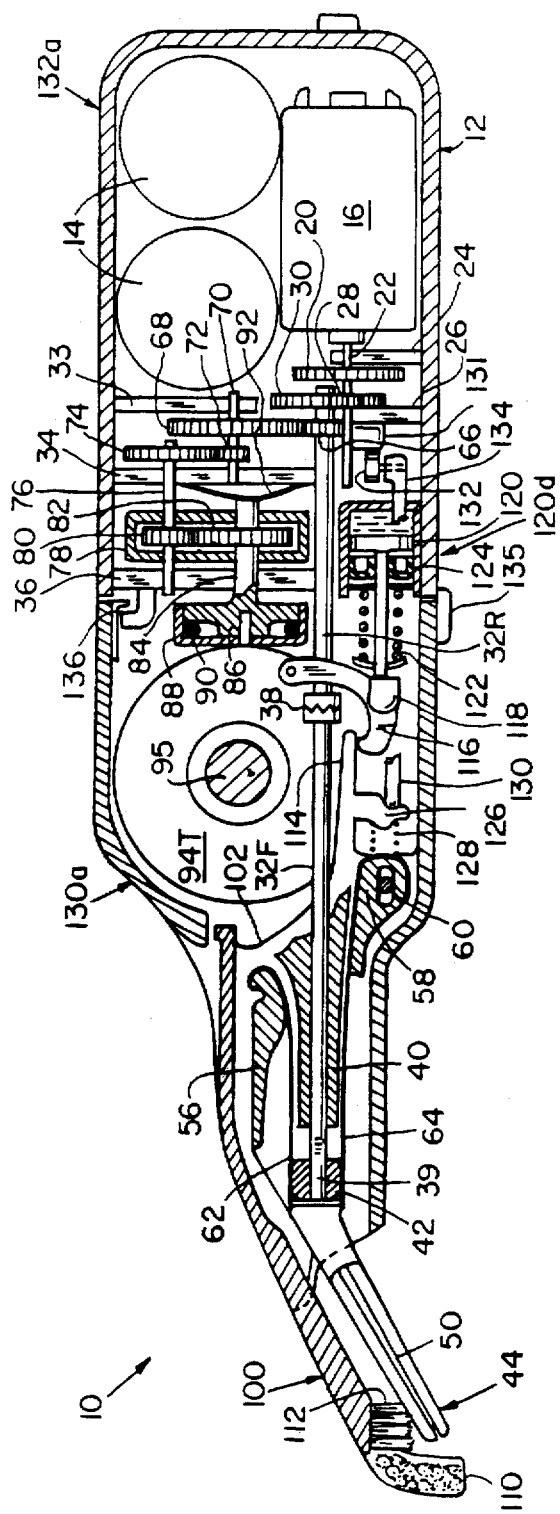
FIG. 2 is a side view, in section, of the dental cleaner of FIG. 1.

A preferred embodiment of an automated dental cleaner embodying the principles of the present invention is shown in FIGS. 1–7 and is identified generally by reference numeral 10. Dental cleaner 10 comprises a hollow elongated housing 12 which encloses two rechargeable batteries 14 (FIG. 2). Conventional electrical connecting means (not shown) connects the batteries for energizing an electric motor 16 to drive the dental cleaner. A conventional electrical switch (not shown) is included in the connecting means for actuating the motor.

A plurality of systems operate various working features of the invention. For organization and clarity, each system is described hereinafter under a heading which identifies each particular system.

Flossing Fork System

Fixedly connected to the motor drive shaft is a pinion 18 (FIG. 3) which is drivingly engaged with a driven gear 20. Gear 20 (FIGS. 2 and 3) is coaxially fixed to an axle 22 which is rotatably supported by bearings 24 and 26. Both bearings are fixed to the housing 12.

A pinion 28, coaxially fixed on axle 22, is drivingly engaged with a driven gear 30 which is coaxially fixed to a rear section of a drive shaft 32R. Shaft section 32R is rotatably supported by bearings 34 and 36 which are fixed to housing 12. The shaft includes a front section 32F rotatably supported by a bearing 40 which is fixed in a narrow front end portion of housing 12. Shaft sections 32F and 32R are coaxially connected by a clutch 38.

A front end portion of shaft section 32F is offset from the main shaft (best seen in FIG. 5) to form a crank 39. A roller 42 is rotatably supported on the crank.

Movably attached to a front end portion of housing 12 is a flossing fork 44 (FIGS. 1–5) having a pair of spaced flossing tines 46 and 48 for receiving teeth to be cleaned therebetween. The tines extend frontward and downward at a slight angle. An outer side of each tine includes a groove 50 (best seen in FIG. 2) which extends longitudinally along the tine and around the distal end portion thereof. The grooves serve as guides for receiving and guiding floss therein. Thus, floss 202 can extend along each tine to span from one tine to the other tine at their distal end portions, thereby forming a floss span 51 between the tines.

A trunk portion of the flossing fork 44 includes spaced opposed side walls 52 and 54 (FIG. 3) which are connected by an upper bridge 56 (FIGS. 2 and 4) and a lower bridge 58. A frontal bridge 59 (FIG. 3) connects walls 52, 54 with the fork tines.

The flossing fork 44 is connected between opposed walls of a U-shaped holder 57 (FIG. 3) by a fork pin 60 received in aligned apertures which pass transversely through the holder and through bridge 58. The aperture through bridge 58 is of oblong cross-section at its outer ends, but narrows to an approximately circular cross-section medially. This allows the distal ends of the flossing fork tines to move in an orbital path.

An elongated upper leaf spring 62 (FIGS. 2, 4 and 5) has a rear end portion fixed to bridge 56. A front end portion of spring 62 rests under tension on the top of bridge 59. An elongated lower leaf spring 64 has a rear end portion fixed to bridge 58. A front end portion of spring 64 rests under tension on the bottom of bridge 59.

Received between and engaging the fork walls 52, 54 and leaf springs 62, 64 is roller 42. When motor 16 is energized, the speed reduction gears drive the crank wherein the crank roller 42 reciprocates flossing fork 44 in an orbital path. The fork being compelled to move in the manner of a second class lever.

If floss span 51 encounters resistance, such as a tight gap between adjacent teeth, the tensioned leaf springs 62, 64 yield vertically to the crank roller. This alters the orbital path of the fork to flatten to a linear side to side motion, thereby allowing the floss span to "saw" its way through the tight gap.

Spool Operating System

A pinion 66 (FIG. 2), coaxially fixed to shaft 32R, drivingly engages a driven gear 68. The gear 68 is coaxially fixed to an axle 70 rotatably supported on bearings 33 and 34.

Coaxially fixed to axle 70 is a pinion 72 which is drivingly engaged with a driven gear 74. The gear 74 is coaxially fixed to an axle 76 rotatably supported on bearings 34 and 36.

Pivotally supported on axle 76 is a transmission case 78 having a first set of aligned apertures which receive the axle therethrough. Case 78 includes a second set of aligned apertures which receive a platen drive shaft 84 which passes through the case. Within case 78 is a pinion 80 coaxially fixed to axle 76. Pinion 80 is drivingly engaged with a driven gear 82 which is within the case and coaxially fixed to shaft 84.

A compression spring 79 (FIG. 1) is positioned between case 78 and housing 12. A nodule projecting from the case is received in an end portion of the spring to keep the same in position. The action of spring 79 is to urge case 78 to pivot about axle 76. That action is opposed by torque urging case 78 to pivot in the opposite direction about axle 76 by the gears when the system is driven. The purpose of the pivoting transmission is explained hereinafter.

As shown in FIG. 2, an end of shaft 84 is coaxially fixed to a platen piston 86 which is housed within a drum-shaped platen 88. An O-ring is positioned between the piston and an annular front plate of the platen. The opposite end of shaft 84 is engaged by the crest of an arcuate leaf spring 92 having end portions fixed to bearing 34.

First and second disks 94S and 94T, respectively, (FIGS. 1 and 2) are rotatably supported to rotate independently of each other on an arbor 95. The arbor is supported by a spool support 97 (FIG. 1) which is fixed to housing 12.

A floss supply spool 96S and a floss take-up spool 96T are rotatably supported on arbor 95 and are detachably fixed to the disks, respectively. Conventional spool holding means such as spring-loaded catches (not shown) allow the spools to be quickly snapped on or off by a user. Being attached to a disk, each spool and its associated disk rotate in unison but independently of the other spool and its associated disk.

Platen 88 drivingly engages both disks (best seen in FIG. 1) and is resiliently urged against the disk rims by spring 92. O-ring 90 evens the contact pressure of the platen on the two disks. When motor 16 is energized, the spools will rotate in opposite directions relative to each other.

Floss 202 from the supply spool 96S may be threaded along guide groove 98 and through the guide groove of each flossing fork tine to form the floss span 51. The floss 202 returns along guide groove 99 to take-up spool 96T.

Hence, when the spools are driven, the floss span 51 is continuously replaced.

The platen serves as a drive wheel with a rotational axis which is movable relative to each disk while the wheel is drivingly engaged with both disks. The rotation ratio between the wheel and each disk is changeable and consequently the rotation ratio between the supply and take-up spools is changeable.

As floss builds up in take-up spool, the floss in the supply spool is reduced. To keep the tension of floss span 51 and its replacement rate constant, the rate at which the two spools is rotated relative to each other requires continuous change. This is due to the changing radii of the wound floss 202 stored on the spools. Under the described conditions, as said radii change, the relative drive resistance of the disks changes accordingly. Hence, a resultant pivotal torque is induced on transmission case 78 in response to the differing resistance of the two disks. When the system is driven, case 78 (and platen 88) will pivot to the position of least resistance. The disk with the spool having the least amount of floss will be engaged further from the platen center than the other disk. Thus, the spool with the least floss will rotate relatively faster than the other spool. As the relative resistance of the disks changes, the transmission case and platen change position accordingly to maintain constant tension and replacement rate of floss span 51.

Bracing and Brushing Fork System and Damping System

Movably mounted to a front end portion of housing 12, above flossing fork 44, is a bracing and brushing fork 100 hereinafter referred to as the BB fork. As shown in the figures, the BB fork 100 comprises a trunk portion 102 having tines 104 and 106 extending frontward and at a slight angle downward therefrom. Extending inward from each tine are brush bristles 110. Extending downward from a medial position at a frontal end portion of trunk 102 is another set of brush bristles 112.

A rear end portion of trunk 102 includes a pair of lugs 108 (FIGS. 6 and 7) extending downward therefrom. Lugs 108 straddle bridge 58 of the flossing fork and each lug includes an oblong aperture aligned with that of bridge 58 to receive pin 60. Hence, the flossing fork and BB fork are movably supported by the same pin wherein the oblong apertures allow forward and back reciprocating movement of the BB fork 100.

Projecting rearward from a rear end portion of trunk 102 (FIG. 2) is a cantilever 114 slidably engaging the lower end of a damper hook 116. The hook is pivotally supported at an upper end portion by a pin fixedly extending from housing 12. Pivotal motion of the hook is guided at a lower portion thereof by U-shaped guide 117 (FIG. 3) molded onto the floor of housing 12.

Extending laterally from the lower portion of the damper hook 116 is a damper lever 118 which is engaged with a rod fixed to the piston 120 of a damper 120d. Also included in the damper 120d is a return spring 122 (FIG. 2) and a fluid seal 124. Other components of the damper 120d are conventional and are not shown.

Figure 6:
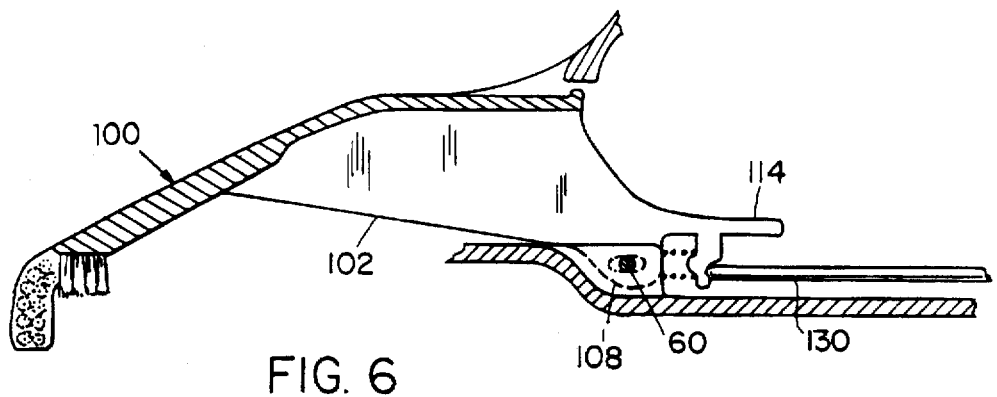
FIG. 6 is a fragmental side view, in section, of the dental cleaner of FIG. 1 showing the bracing and brushing fork connected to the cleaner housing and engaged by a push rod that drives the fork.
Figure 7:
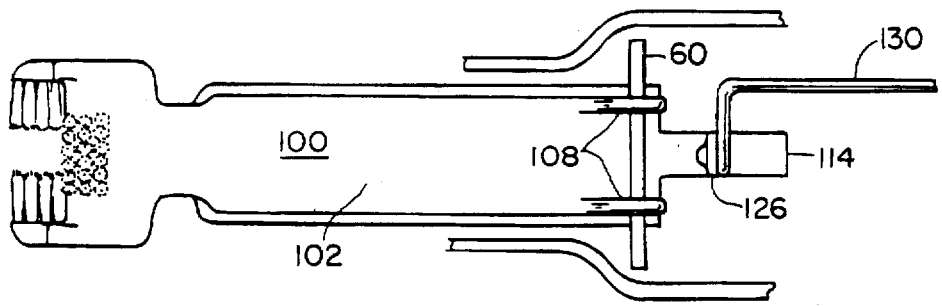
FIG. 7 is a fragmental bottom view, partly in section, of the dental cleaner of FIG. 1 showing the bracing and brushing fork connected to the cleaner housing and engaged by the push rod that drives the fork.
Figure 8:
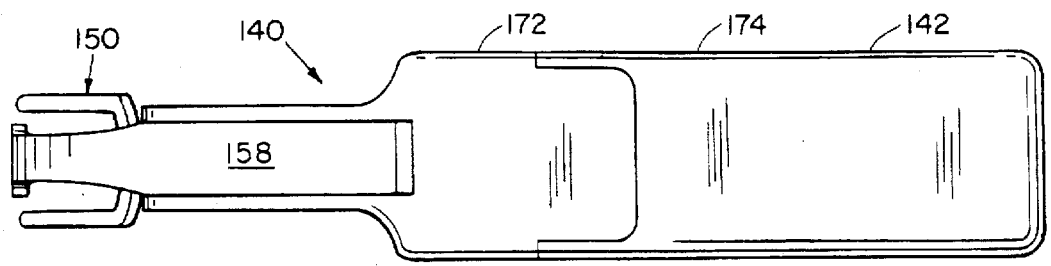
FIG. 8 is a top view of another preferred dental cleaner.
Figure 9:
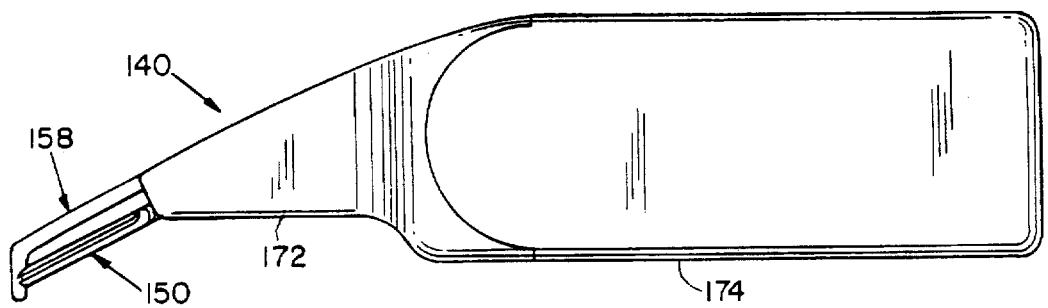
FIG. 9 is a side view of the dental cleaner of FIG. 8.
Figure 11:
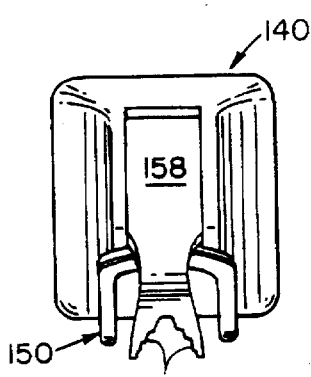
FIG. 11 is a front view of the dental cleaner of FIG. 8.
Figure 10:
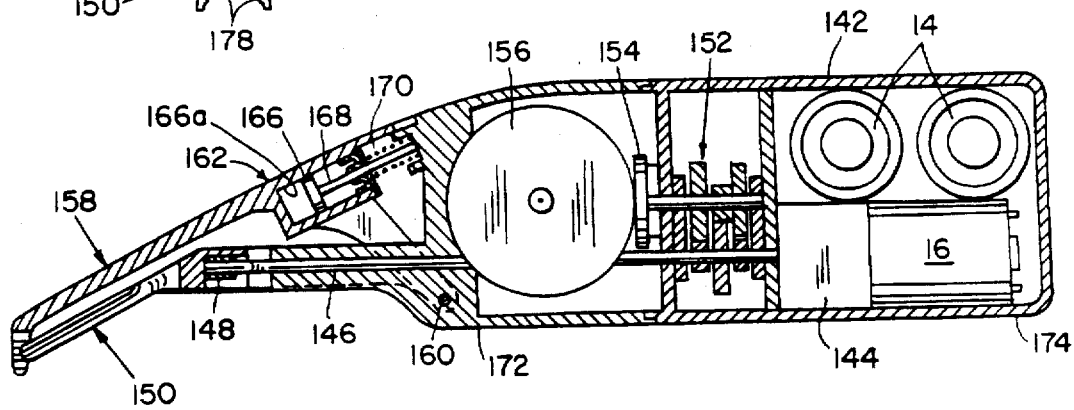
FIG. 10 is a side view, in section, of the dental cleaner of FIG. 8.

Extending downward from cantilever 114 is a thrust receiver 126. A front side of the thrust receiver includes a nodule which is received in the end portion of a compression spring 128 (FIG. 2). The opposite end of the spring is fixed to housing 12. A rear side of the thrust receiver is indented to receive an L-shaped front end portion of a push rod 130 (FIG. 2, 6 and 7). Rod 130 is slidably supported for longitudinal reciprocating movement by guides molded onto the floor of housing 12.

Cantilever 114 and thrust receiver 126 are molded together with the BB fork 100 as a one piece unit.

Figure 3:
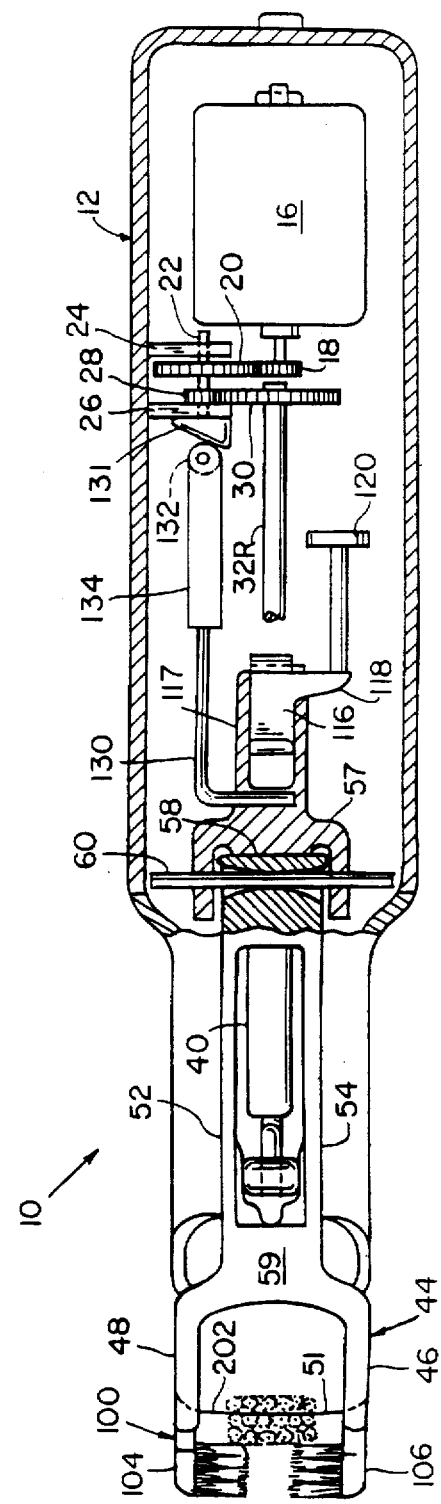
FIG. 3 is a bottom view, partly in section, of the dental cleaner of FIG. 1 with some parts removed.
Figure 4:
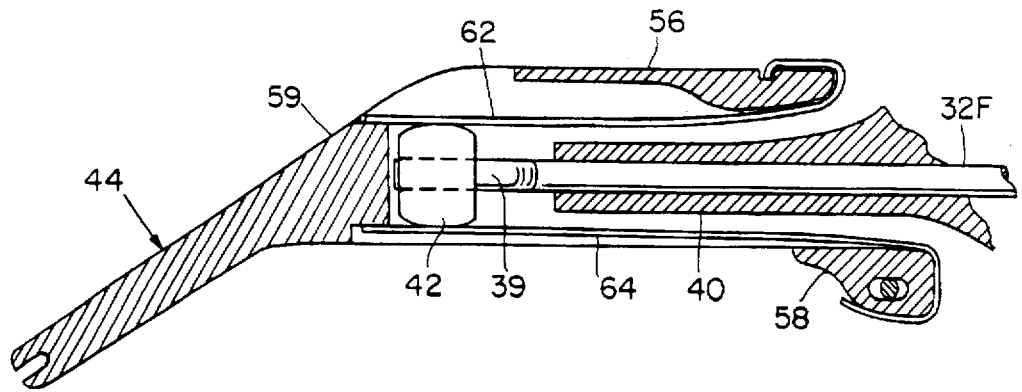
FIG. 4 is an expanded fragmental side view, in section, of the cleaner of FIG. 1 showing the flossing fork with leaf springs engaged by a roller on a crank that reciprocates the fork.
Figure 5:
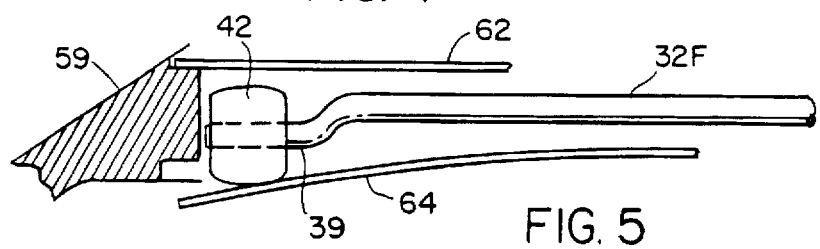
FIG. 5 is the view of FIG. 4, further fragmented, showing the crank and roller in a different position and one of the leaf springs yielding as the flossing fork encounters resistance.

A cam 131 is coaxially fixed to axle 22 (FIGS. 2 and 3). The cam engages a roller 132 which is rotatably supported by a pin on a cam follower 134. The follower 134 is supported for longitudinal reciprocating movement as the cam is driven by motor 16. A front end of the follower 134 engages a rear end of push rod 130.

When motor 16 is energized, cam follower 134, rod 130, and the BB fork, are cyclically moved forward by cam 131. Spring 128 returns them back after each forward motion. Hence, the brushes all reciprocate forward and back.

When cleaning teeth, the brushes engage and scrub three dental surfaces simultaneously; the lingual, buccal, and top surfaces. The flexible BB fork tines allow the fork to adjust to teeth of various sizes so that all three brushes are engaged with teeth. Brushing and flossing are achieved at the same time.

The BB fork 100 also inhibits lateral motion of the front end of the dental cleaner. This is especially important when the floss encounters tight interdental gaps. As described hereinbefore, under the Flossing Fork System heading, the floss span 51 can "saw" its way through tight interdental gaps. To prevent the floss from getting caught in these gaps, the BB fork 100 braces the front end of the dental cleaner on the teeth being flossed. The added leverage overcomes tight gap resistance.

Damage to gingival tissue occurs often in hand flossing when the floss is snapped through a tight spot between teeth and motion continues until stopped by impact with the gingival tissue between the teeth. This damage can be serious especially if done repeatedly which it often is because of the poor control over the floss span in most situations. Commercially available flossing aids including motorized devices can actually make the problem worse by causing the operator to force the floss through the tight areas with force of the hand but at a greater distance from the resistance so that the ability to control the floss precisely is reduced. A major feature of the present invention is a mechanism that aids floss control and prevents damage to gingival tissue caused by excessive force pushing the floss span into the tissue.

In the present invention, the BB fork 100 in concert with the damper 120d prevent sudden floss-thrusts against gums. Upon entry of the floss span 51 into an interdental gap, the BB fork brush 112 engages an adjacent tooth and the BB fork 100 begins to pivot about pin 60. As the BB fork 100 pivots, cantilever 114 pivots damper hook 116 wherein its damper lever 118 pushes the damper piston 120. Rapid pivotal motion is thus dampened so that rapid vertical thrusts into interdental spaces are prevented. Access of the floss to the full depth of interdental spaces is allowed at a safe insertion rate.

Other Features

Dental cleaner 10 is designed to be disassembled by the user into two sections; a front section 130a (FIG. 2) and a rear of back section 132a. Means for quick detachment and reassembly of the two sections include a conventional latch 135 and a separable hook hinge 136.

When the two sections 130a and 132a separate, drive shaft 32R, platen 88, cam follower 134, and the damper 120d disengage from components in the front section 130a to remain with the back section 132a. The motor 16, batteries 14, and drive transmissions also remain in the back section 132a. Forks 44, 100 and spools 96S, 96T stay with the front section 130a.

Separation of the two sections 130a and 132a exposes the spools 96S and 96T so the floss supply spool 96S can be replaced by a new one. A fully-loaded take-up spool 96T can be discarded and the empty supply spool can be used as a new take-up spool.

To reassemble the two sections 130a and 132a, the hinge 136 is hooked together first. The sections 130a and 132a are then pushed together and latch 135 is closed. Closing the sections 130a and 132a together engages all the drive systems. Spring 92 is tensioned by the pressure of platen shaft 84 as the platen engages the disks.

For hygienic reasons, the invention may be sold with multiple front sections 130a, each for a household user. The more costly back section 132a does not enter the oral cavity and can be shared by all household users.

Other Preferred Embodiments

Referring to FIGS. 8–11, dental cleaner 140 is another preferred embodiment of the present invention. Dental cleaner 140 includes features that function in a similar manner as those of dental cleaner 10. Dental cleaner 140 has a hollow housing 142 containing batteries 14 for energizing a motor 16. The motor drives a transmission 144 for rotating a drive shaft 146. A front end portion of the drive shaft includes a crank having a roller 148 which engages and drives a flossing fork 150 in an orbital path.

Transmission 144 also drives a platen drive transmission 152 which, in turn, drives a platen 154. A pair of floss spools 156, mated with disks, are driven by the platen in the same manner as in dental cleaner 10.

The dental cleaner 140 also includes a bracing fork 158 for bracing the dental cleaner 140 on teeth being flossed by the flossing fork 150. Both forks 150, 158 are movably connected to housing 142 by a fork pin 160.

A notable difference between dental cleaner 140 and dental cleaner 10 is the location of the bracing fork dashpot or damper 162 on dental cleaner 140. The damper cylinder 166a is molded in unison with the trunk of the bracing fork 150. A damper piston 166 is fixed to a piston rod 168 having an end which engages housing 142. Piston 166 moves within the damper 162 when the bracing fork 158 pivots about pin 160. Hence, the function of the damper 162 is the same as the damper in dental cleaner 10. The bracing fork 158 is urged back to its initial operation position by a compression spring 170 positioned between the damper 162 and housing 142. When the front section 172 of housing 142 is detached from the back section 174, the damper 162 stays with the front section 172.

Another difference between dental cleaner 140 and dental cleaner 10 is that the bracing fork 158 of dental cleaner 140 is without brush bristles. The tines 178 (FIG. 11) of the fork are bracing tines for bracing the dental cleaner 140 on a tooth. Edges of the tines 178 brace the dental cleaner on a tooth and are serrated for gripping thereon. To straddle and brace onto teeth of various types and sizes, the bracing tines 178 diverge with increasing distance from each other as the distance toward their distal ends increases.

Figure 12:
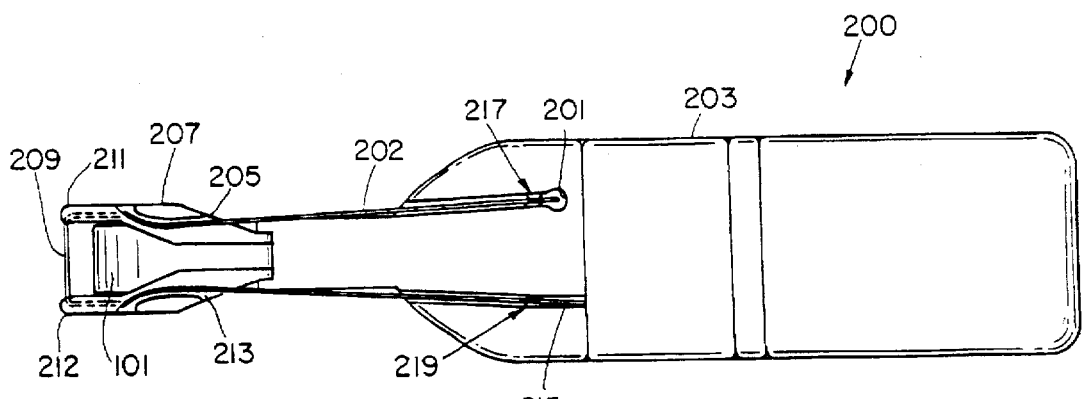
FIG. 12 is a top view of still another preferred dental cleaner.
Figure 15:
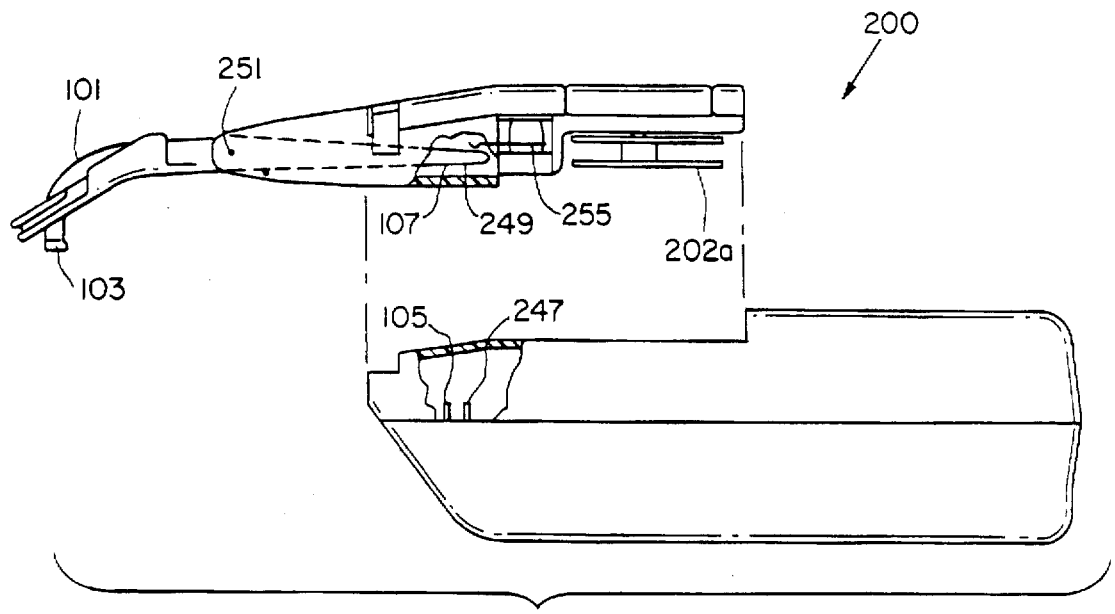
FIG. 15 is a side view of the dental cleaner depicted in FIG. 12 with the fork assembly separated from the body assembly.
Figure 16:
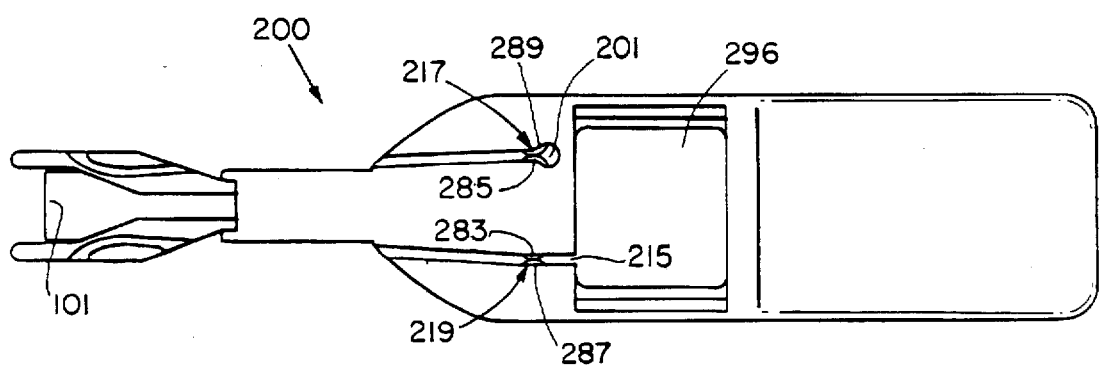
FIG. 16 is a top view of the dental cleaner depicted in FIG. 12 with the top cover removed to show the compartment for collecting used dental floss.
Figure 17:
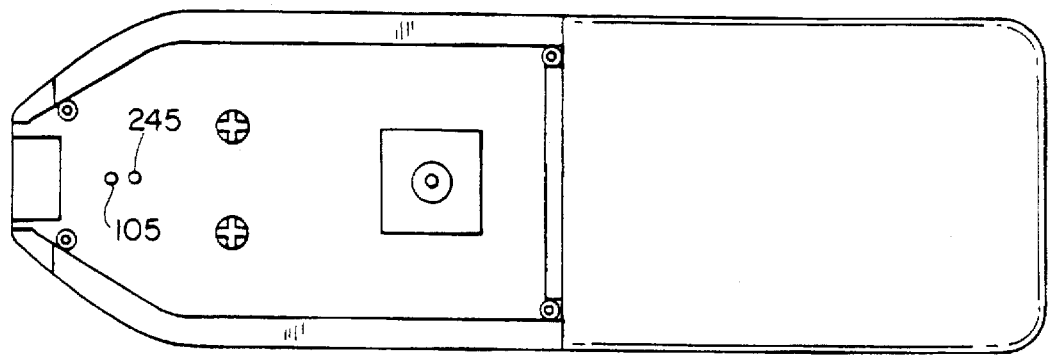
FIG. 17 is a top view of the body assembly of FIG. 15.

FIGS. 12–23 depict still another preferred embodiment of the present invention. Dental cleaner 200 extends floss 202 (FIGS. 12 and 13) from a supply spool 202a (FIG. 15) through a supply port 201 (FIG. 12) in body 203, through channel 205 in floss fork 207, across the tines 211 and 212 of floss fork 207, through channel 213 and through return port 215 into used floss storage compartment 296 (FIG. 16). This forms a span 209 of dental floss across tines 211 and 212 (FIG. 12). A pair of supply rollers 217 hold floss 202 in tension against a pair of return rollers 219.

Figure 13:
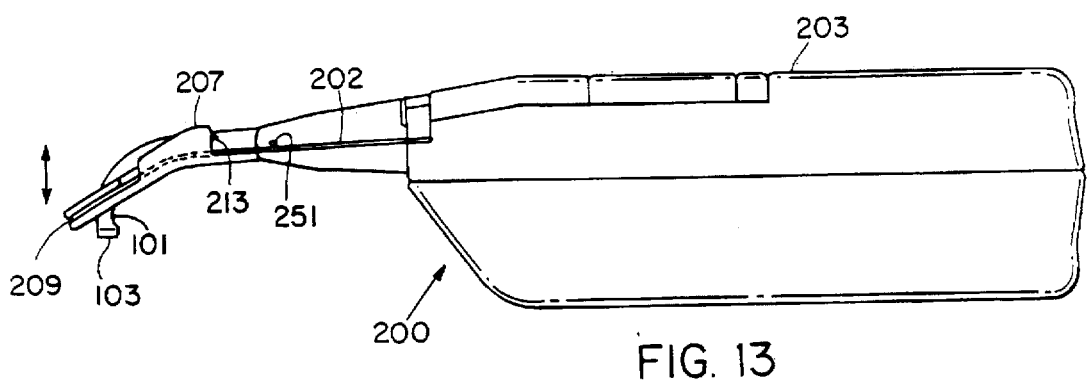
FIG. 13 is a side view of the dental cleaner depicted in FIG. 12.
Figure 14:
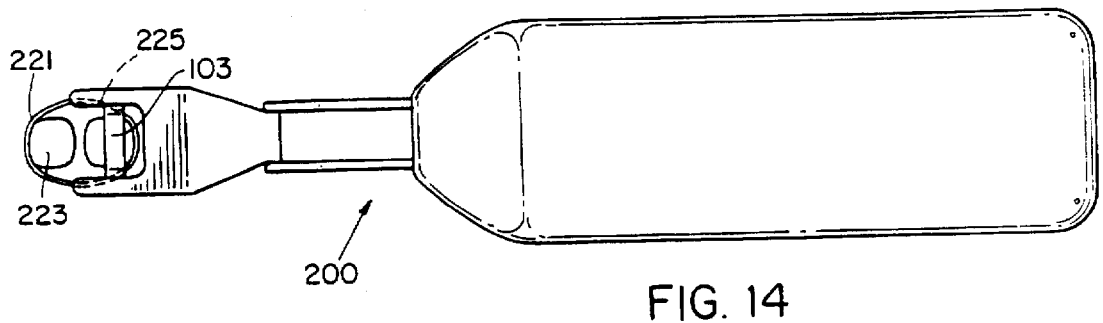
FIG. 14 is a bottom view of the dental cleaner depicted in FIG. 12.

In operation, the tines of floss fork 207 can reciprocate vertically as seen in FIG. 13 for vertical movement of floss span 209. The supply rollers 217 and return rollers 219 grip the floss 202 by pinching it between the pairs of rollers and provide longitudinal movement of floss span 209. The floss 202 (including the floss span 209) can travel in one direction a fixed distance then travel in the opposite direction a fixed distance to longitudinally oscillate the floss span. The oscillation is unbalanced such that the floss moving from the supply rollers 217 to the return rollers 219 travels a greater distance than when the floss moves from the return rollers 219 to supply rollers 217. This results in a net translation of the floss 202 from tine 211 to tine 212. As a result, the floss 202 in span 209 is continuously renewed.

Cleaning below the gum line requires forming a loop 221 (FIG. 14) in the span 209 of floss around a tooth 223. A loop 225 can also be formed in the span 209 of floss in the opposite direction. Forming either loop 221 or 225 requires pulling more floss 202 from the supply rollers 217. The drive of dental cleaner 200 allows such loops to be formed. Additionally, changing from a loop of floss to a straight span requires rapid take up of the slack dental floss. This is also accommodated by the drive of dental cleaner 200. When the span 209 is being inserted into a gap between teeth that is small and provides resistance to the floss, it is desirable to "saw" the floss through the tight region of the gap using only the longitudinal motion of the floss in span 209. This means the vertical motion of floss fork 207 must stop and only the motion provided by drive roller pairs 217 and 219 will continue. The same condition exists upon removal of the span 209 through the same tight area.

Figure 18:
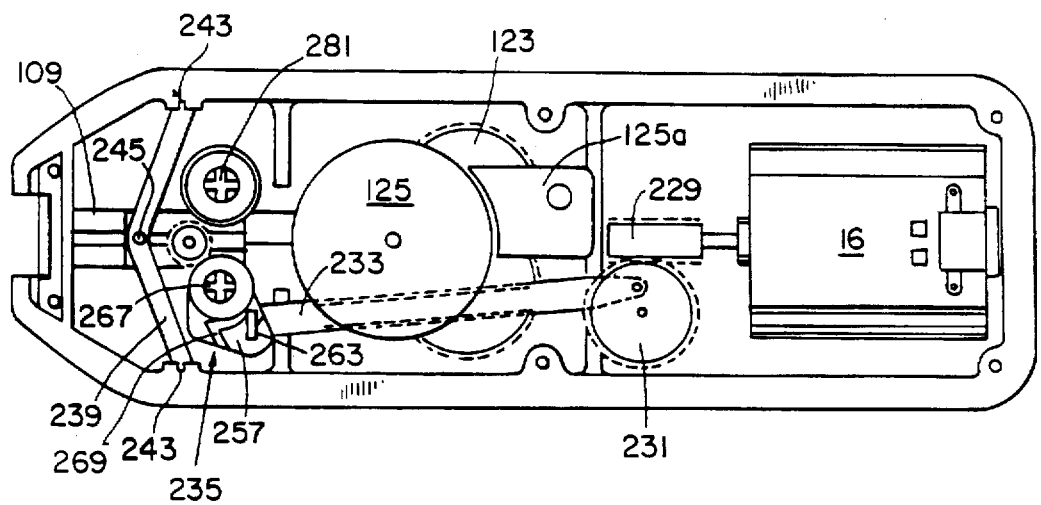
FIG. 18 is a top sectional view of the body assembly of FIG. 17 showing the drive linkage.
Figure 19:
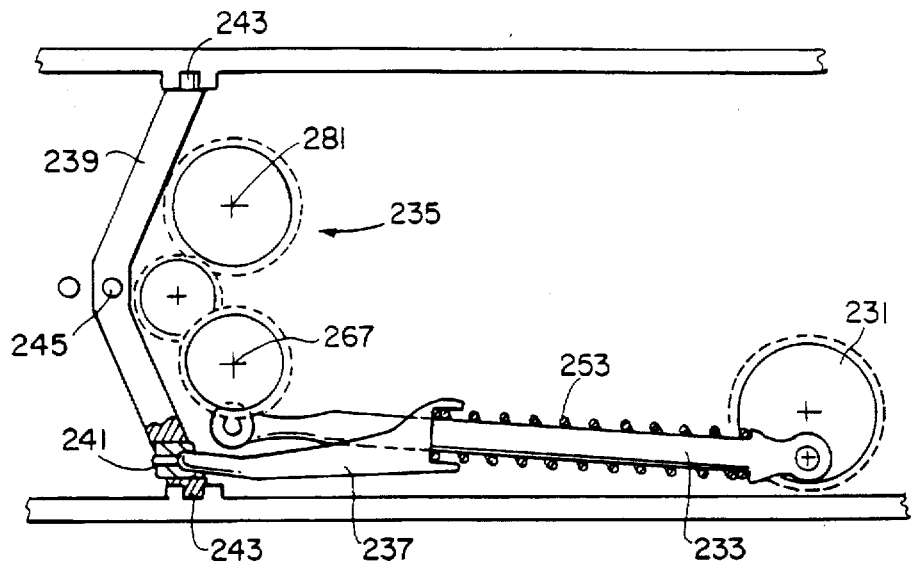
FIG. 19 is an enlarged view of the drive linkage depicted in FIG. 18.
Figure 20:
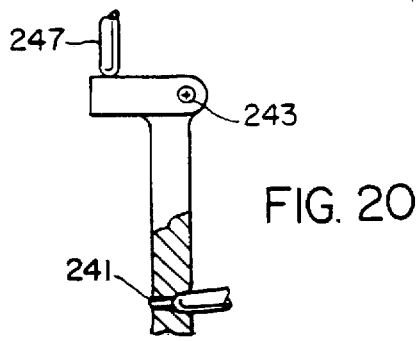
FIG. 20 is an enlarged side view of link 239.

The floss supply rollers 217, floss return rollers 219 and floss fork 207 are driven by an electric motor 16 (FIG. 18). A worm 229 is coupled to the output shaft of motor 16 for driving a worm gear 231. Connecting rod 233 is coupled to worm gear 231 for driving transmission 235. The reciprocating action of rod 233 drives link 237 (FIG. 19) which engages link 239 via ball joint 241 and oscillates link 239 about pivots 243 creating a reciprocating motion at point 245. This drives pin 247 (FIG. 20) which engages floss fork 207 at point 249 (FIG. 15) and oscillates floss fork 207 about pin 251 (FIG. 13) to provide vertical movement of floss span 209.

A spring 253 (FIG. 19) disposed about rod 233 and contacting link 237 limits the force that can be applied to the floss fork 207 so that reciprocating motion of floss fork 207 will stop when the lateral force on floss span 209 exceeds a fixed amount. Floss fork 207 is driven only on the forward stroke with the return stroke being provided by a return spring 255 (FIG. 15). The force exerted by spring 253 must be sufficient to overcome the force of return spring 255 as well as the preset load that can be applied to the floss span 209.

Figure 21:
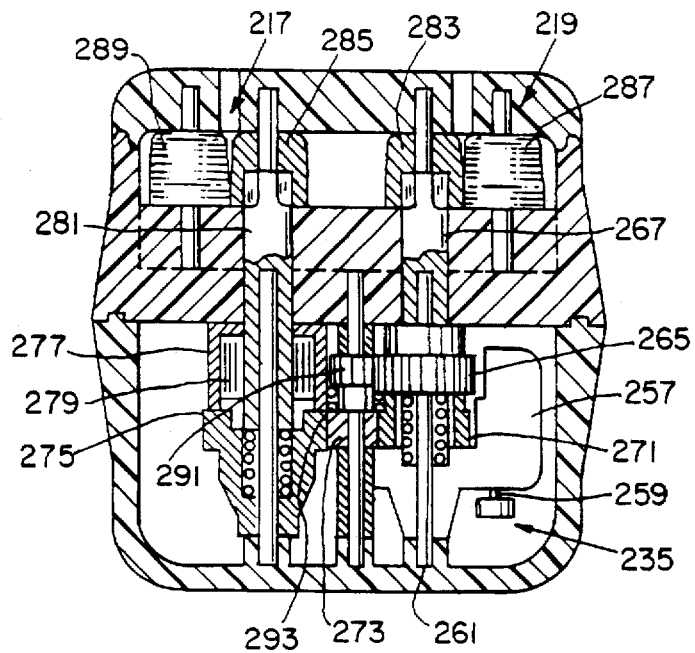
FIG. 21 is a cross-sectional view of the body assembly of FIG. 15 showing the transmission assembly.
Figure 22:
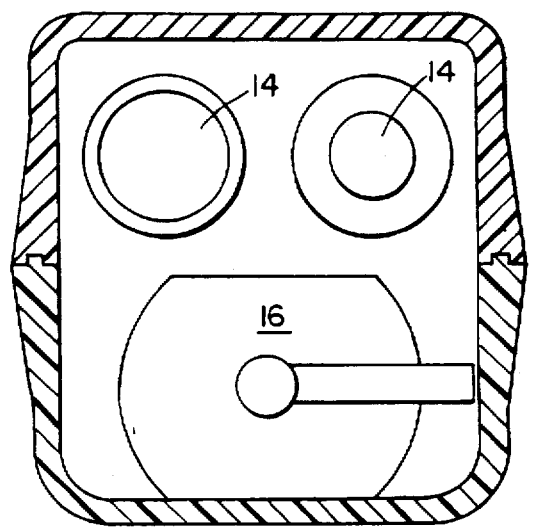
FIG. 22 is a cross-sectional view of the body assembly of FIG. 15 showing the motor and batteries.

Transmission 235 (FIG. 21) drives supply rollers 217 and return rollers 219. Transmission 235 has 5 gears, two rachet drives and 2 clutches on three parallel shafts. Rod 233 (FIGS. 18 and 19) drives rachet assembly 257 via pin 259 (FIG. 21) so that rachet assembly 257 reciprocates in approximately a 90° arc about shaft 261. When rotating in a counter clockwise direction as viewed from above (FIG. 18) rachet pawl 263 rotates gear 265 (FIG. 21) to drive roller shaft 267 counter clockwise approximately 90°. When rotating in a clockwise direction rachet pawl 269 (FIG. 18) engages gear 271 (FIG. 21). Gear 271 drives gear 273 which drives gear 275 in a clockwise direction. Gear 275 drives housing 277 which engages the OD of spring 279 winding spring 279 to create a torque on shaft 281 which engages the inner coil of spring 279. Spring 279 and housing 277 form a spring clutch. This reciprocates the active floss drive rollers 285 and 283 of supply rollers 217 and return rollers 219, respectively. The passive rollers 289 and 287 of supply rollers 217 and return rollers 219 are driven by the active rollers preferably via meshed gear teeth on the rollers or alternatively by friction. The floss 202 is driven by the friction created by being squeezed between the rollers 217 and 219.

When the floss 202 is pulled by one set of rollers, the other set provides resistance to generate tension in the floss 202. When roller 283 is driven in the counter clockwise direction pulling the floss 202, roller 285 provides the resistance. As the floss 202 is pulled against roller 285, shaft 281 turns winding spring 279 to create a torque in housing 277 and gear 275. Gear 275 drives gear 271 through gear 273 at approximately 1.3 times the speed of gear 275. Gear 271 can only go the same speed as the rachet pawl that engages it and thus the same speed as gear 265 and roller 283. In the attempt of gear 275 to overdrive gear 271, a resistance is created in the movement of gear 275 which creates a torque through spring 279 on shaft 281 and roller 285. Thus, moving floss 202 in the forward direction (counter clockwise at roller 283) winds spring 279. Spring 279 can slip relative to housing 277 if it is wound beyond a preset torque. This assures a tension in the floss 202 and allows the floss 202 to be pulled out at will at a tension that causes the spring clutch (spring 279 and housing 277) to slip.

When roller 285 is driven clockwise to pull the floss in the reverse direction, roller 283 provides the resistance that maintains the floss tension. The floss tension drives roller 283 clockwise which drives gear 265 clockwise via shaft 267. Gear 265 drives gear 291. Gear 273 is driven in this mode by gear 271. Gear 265 is larger than gear 271 and gear 291 is smaller than gear 273. Gear 291 and gear 273 are connected via spring 293. When gear 291 attempts to drive gear 273 counter clockwise, spring 293, held at one end by gear 273, wraps tightly around a cylindrical section of gear 291 to lock gear 291 to gear 273. Thus, when gear 265 driven by the floss attempts to drive gear 291 faster than gear 271 is driving gear 273, a resistance is created that provides the floss tension.

When gear 265 is driven by rachet pawl 263, the spring clutch formed by gear 291, spring 293 and gear 273 slips allowing gear 291 to rotate freely relative to gear 273 to allow free motion of gear 265.

The floss 202 is typically advanced 0.2 inches forward and 0.15 inches backward on each stroke at a frequency of about 2 strokes per second. Transmission 235 is not only capable of reciprocating the floss but is also capable of taking up slack floss and allowing floss to be pulled slack due to springs 279 and 293.

Figure 23:
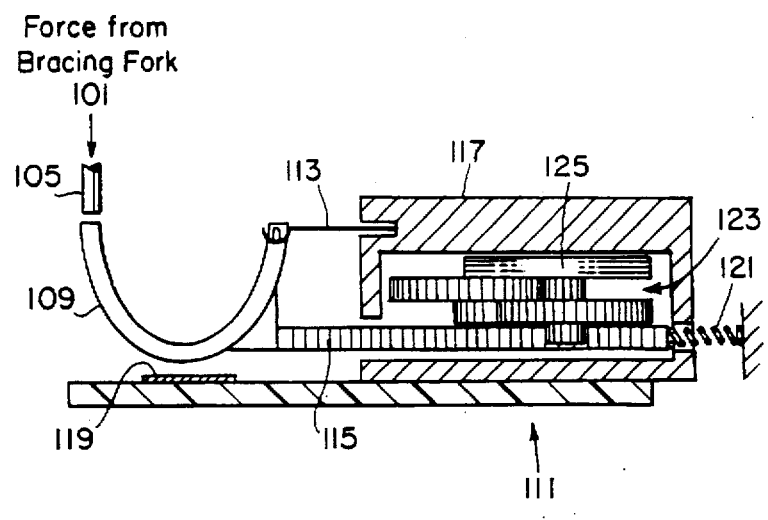
FIG. 23 is a side sectional view of the inertial damping system for the dental cleaner of FIG. 12.

Dental cleaner 200 also includes a bracing fork 101 which has a generally V-shaped end 103 which rides on the teeth adjacent to the gap engaged by the floss. The bracing fork 101 pivots about pin 251 and in operation is spring loaded to maintain the V-shaped end 103 firmly on the teeth. This prevents motion of the end of dental cleaner 200 that would otherwise occur as a reaction to the forces exerted by the teeth on the floss span 209 especially when the span 209 is sawing through a tight spot. The other end of bracing fork 101 (FIGS. 12, 13, 15 and 16) engages pin 105 at area 107 (FIG. 15). Pin 105 transfers upward forces (as viewed in FIGS. 13–15) exerted on the end of V-shaped end 103 to downward forces on lever 109 (FIG. 23).

Motion of the bracing fork 101 relative to body of dental cleaner 200 and floss fork 207 is regulated by inertial damping system 111. Inertial damping system 111 provides inertial resistance to the movement of bracing fork 101 in normal operation and if bracing fork 101 is excessively loaded at V shaped end 103, the resultant motion will be limited, which limits the speed with which the floss fork 207 can drive floss span 209 between teeth and into the gum. The system also adds a feel of stability to dental cleaner 200 in operation.

Lever 109 is held in position by spring 113 and rack 115. Spring 113 is fixed in gear housing 117 at one end and lever 109 is pivotably attached at the opposite end. One end of rack 115 is in contact with lever 109 and prevents free rotation of lever 109. Lever 109 is normally held above friction pad 119 by spring 113. A downward force below a preset limit exerted by pin 105 will cause rotation of lever 109 about the end of spring 113 causing rack 115 to move to the right. Rack 115 is forced to the left by spring 121 to maintain the position of lever 109 and in turn bracing fork 101. Rack 115 is meshed with a gear train 123 which amplifies the motion of rack 115 and rotates mass 125 when rack 115 is moved to the right. A clutch disengages rack 115 from mass 125 when rack 115 moves to the left. A brake 125a (FIG. 18) can be included to brake mass 125. By this mechanism, a force on rack 115 to the right rotationally accelerates mass 125, thereby providing damped resistance. A downward force above a preset limit on lever 109 will exert a force on rack 115 that will be met by an equal resistance delaying the rotation of lever 109 about the end of spring 113. This causes lever 109 to be forced downward with sufficient force to bend spring 113 and allow the midsection of lever 109 to be driven into friction pad 119, thereby, severely limiting or stopping the motion of lever 109 and in turn bracing fork 101. Stopping the motion of bracing fork 101 stops the movement of the entire dental cleaner 200 relative to the teeth and this prevents floss fork 207 from driving floss span 209 into the gum. Therefore, by this mechanism, when floss span 209 is being forced between teeth and suddenly slips free, the force is immediately transferred to the bracing fork 101, which will resist the force and lock up if the force is excessive, preventing floss span 209 from being driven into the gum. Yet, when the motion is halted and the force reduced, the floss span 209 can be guided under the gum line because the bracing fork will be free to move.

Figure 24:
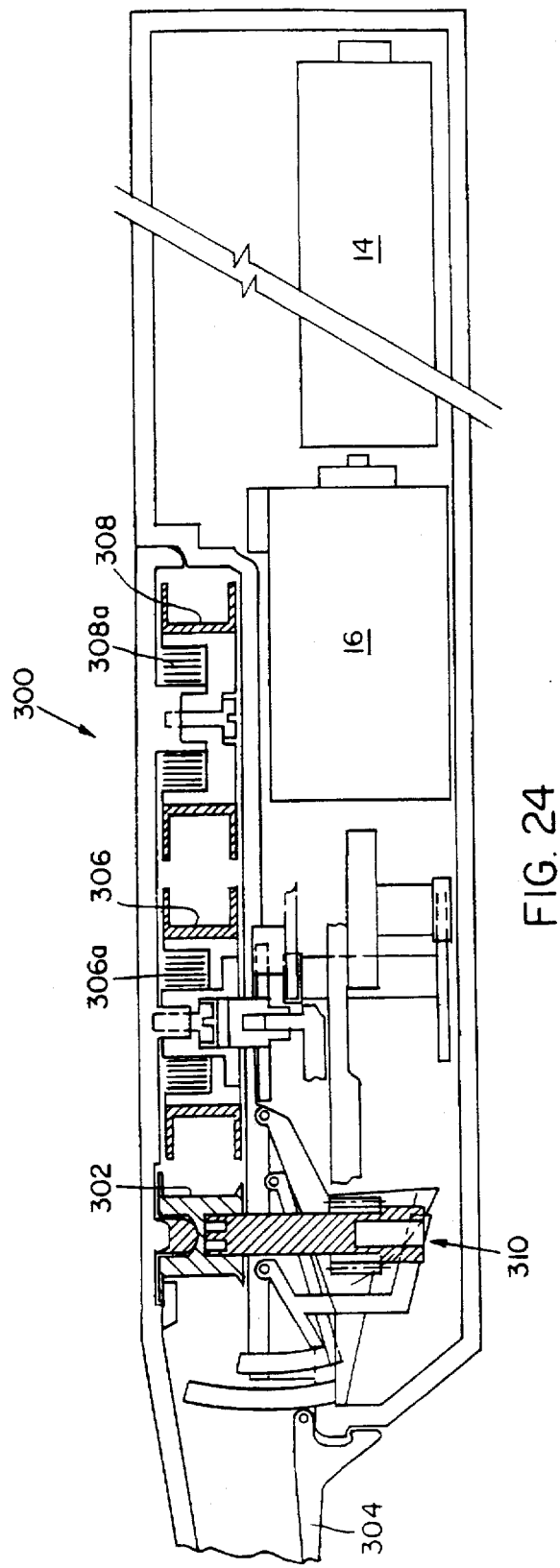
FIG. 24 is a side sectional view of another preferred dental cleaner.

FIG. 24 depicts another preferred embodiment of the present invention. Dental cleaner 300 is similar to dental cleaner 200 differing mainly in that the floss 202 is driven by two capstans 302, one for supplying floss and another for returning floss rather than by two pairs of pinch rollers. Sufficient friction between the capstans and the floss 202 for driving the floss 202 is provided by wrapping the floss 202 around each capstan 302 two turns. The supply and return spools 308 and 306 are located in line with each other. Floss fork 304 is driven by drive 310. Drive 310 is functionally similar to the drive that drives floss fork 207 of dental cleaner 200.

Figure 25:
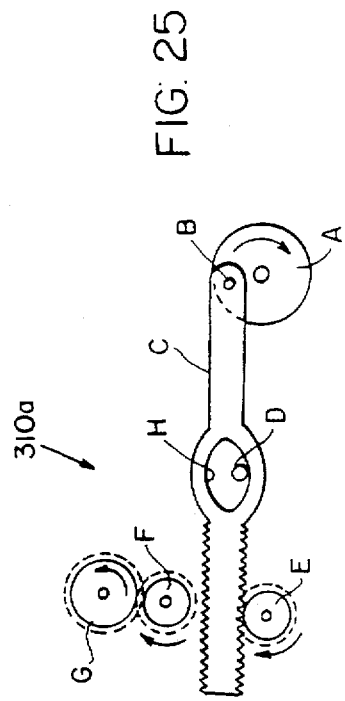
FIG. 25 is a simplified drawing of a portion of the drive for the dental cleaner of FIG. 24.

Referring to FIG. 25, capstans 302 are driven by drive 310a. Gear A is driven in a clockwise direction by the motor through a gear reduction such as a worm gear. Rack C is coupled to gear A by pin B at a location offset from the center of rotation of gear A, thereby forming a crank to drive rack C. Gear A drives rack C in an orbital motion guided by pin D and the interactions with gear E and F. Gears E and G drive capstans 302 via connecting shafts. Gear F reverses the motion imparted by rack C to obtain the correct motion of Gear G. Hole H in rack C is shaped to alternatively engage rack C to gear E and gear F.

In the position shown in FIG. 25, gear A is driving rack C to the right and rack C is held engaged to gear E by pin B and pin D in conjunction with shaped hole H which acts as a cam surface. Gear E rotates clockwise and will continue to be rotated clockwise until rack C is pulled as far right as possible. At that point, the left side of hole H will engage pin D and as gear A continues to rotate moving pin B downward, rack C will rotate about pin D so that gear F is engaged. As gear A continues to further rotate, rack C is driven to the left and rotates gear F clockwise which in turn rotates gear G counter-clockwise. When pin B is in its extreme left position, the right side of hole H engages pin D and rack C is moved back into engagement with gear E.

Gear E drives the return capstan and gear G drives the supply capstan. Gear G is larger than gear E and, therefore, rotates fewer degrees than gear E. Thus, the floss is driven further in the return direction than the supply direction so that for each cycle of motion, a net movement results from supply to return.

An important feature of this transmission is that when one gear is driven, the other is free to rotate. When gear E is driving the return capstan, the supply capstan driven by gear G is free to rotate to allow floss to be pulled directly from the supply spool 308 (FIG. 24). The rotation of the supply spool 308 is restricted by a clutch and power spring 308a. The action of the floss pulling on the spool 308 rotates the spool against the resistance of the power spring and winds the power spring until the clutch begins to slip. By this means, a tension is maintained on the floss 202 as the floss is pulled by the return capstan. If a loop of floss is pulled and released, the spring first unwinds, then rewinds to quickly return tension to the floss. Maintenance of tension is not only important during the forward motion of the floss but also for the return motion. When the supply capstan is rotating in reverse and feeding floss back to the supply spool, tension is required between the spool and capstan to maintain the frictional grip between the capstan and the floss. When the capstan is rotated in reverse, the spool is rotated by the power spring to maintain the required tension.

The return spool 306 must maintain tension on the floss between the return spool and the return capstan. The return spool 306 is driven by the motor through a gear reduction. A power spring and clutch 306a are between the spool and shaft that is driven by the motor. The driving shaft winds the spring until the clutch slips so that a tension is maintained even though the forward motion of the capstan may momentarily exceed the driving speed of the spool. Tension is also maintained when the return capstan drive is disengaged as the supply capstan is being driven. If a loop is pulled in the floss, the spring will quickly take up the slack and restore tension when the supply capstan is being driven.

While the above description contains many specifications, these should not be construed as limitations on the scope of the invention, but rather as an exemplifications of preferred embodiments. Those skilled in the art will envision other possible variations that are within its scope. Each embodiment described above may include various features from the other embodiments. Accordingly, the scope of the invention should be determined not be the embodiments illustrated, but by the appended claims and their legal equivalents.

What is claimed is:

1. A dental cleaner comprising:
    a fork having a pair of tines for receiving teeth to be cleaned therebetween;
    first and second brushes, each brush being attached to a respective tine and having bristles extending inward between the tines for engaging lingual and buccal tooth surfaces simultaneously;
    a third brush attached to the fork and having bristles extending medially thereof for engaging tooth top surfaces; and
    a drive mechanism for reciprocating each of the first, second and third brushes in a back-and-forth linear motion.

2. The dental cleaner as defined in claim 1, wherein the fork is detachably removable from the drive.

3. The dental cleaner of claim 1, further comprising a pair of flossing tines for supporting therebetween a span of dental floss substantially perpendicular to the longitudinal axis of the drive.

4. The dental cleaner of claim 3, further comprising a limiting system for limiting the motion of the flossing tines in response to resistance encountered in use.

5. A dental cleaner comprising:
    a fork having a pair of tines for receiving teeth to be cleaned therebetween;
    first and second brushes, each brush being attached to a respective tine and each brush having bristles extending inward between the tines for simultaneously engaging lingual and buccal tooth surfaces; and
    a drive for reciprocating the first and second brushes in a back-and-forth linear motion.

6. The dental cleaner as defined in claim 5, further comprising a third brush attached to the fork and having bristles extending medially thereof for engaging tooth top surfaces, the third brush being connected to the drive for being reciprocated.

7. The dental cleaner as defined in claim 5, further comprising a pair of flossing tines for supporting therebetween a span of dental floss substantially perpendicular to the longitudinal axis of the drive.

8. The dental cleaner as defined in claim 7, further comprising a limiting system for limiting the motion of the flossing tines in response to resistance encountered in use.

9. A dental cleaner comprising:

a housing;

a fork supported on the housing having a pair of spaced tines for receiving teeth to be cleaned therebetween;

first and second brushes attached to the tines, respectively, the brushes having bristles extending inward between the tines for simultaneously engaging lingual and buccal tooth surfaces, thereby bracing the fork against the teeth; and a drive for driving the dental cleaner and inducing a cleaning motion to the bristles, the drive including a cam for moving the brushes in a forward linear motion, and a spring for biasing the brushes back in a rearward linear motion.

10. The dental cleaner as defined in claim 9, wherein the bristles are of differing lengths.

11. The dental cleaner of claim 9, further comprising a pair of flossing tines for supporting therebetween a span of dental floss substantially perpendicular to the longitudinal axis of the drive.

12. The dental cleaner of claims 11, further comprising a limiting system for limiting the motion of the flossing tines in response to resistance encountered in use.

* * * * *